(12) United States Patent
Kolyadko et al.

(10) Patent No.: US 10,006,080 B2
(45) Date of Patent: Jun. 26, 2018

(54) HIGH-SELECTIVITY CONTACT ACTIVATION INHIBITOR BASED ON INFESTIN-4

(71) Applicant: OBSCHESTVO S OGRANICHENNOY OTVETSTVENNOSTYU "GEMATOLOGICHESKAYA KORPORATSIYA", Moscow (RU)

(72) Inventors: Vladimir Nikolaevich Kolyadko, g. Zelenograd (RU); Fazoil Inoyatovich Ataullakhanov, Moscow (RU); Mikhail Aleksandrovich Panteleev, g. Mytishchi (RU); Tatyana Alekseevna Vuymo, Moscow (RU); Ruzanna Armenovna Ovsepyan, g. Puschino (RU); Stepan Sergeevich Surov, g. Korolev (RU); Vera Anatoljevna Korneeva, g. Himki (RU)

(73) Assignee: OBSCHESTVO S OGRANICHENNOY OTVETSTVENNOSTYU "GEMATOLOGICHESKAYA KORPORATSIYA", Moscow (RU)

( * ) Notice: Subject to any disclaimer, the term of this patent is extended or adjusted under 35 U.S.C. 154(b) by 0 days. days.

(21) Appl. No.: 15/038,819

(22) PCT Filed: Nov. 25, 2014

(86) PCT No.: PCT/RU2014/000889
§ 371 (c)(1),
(2) Date: May 24, 2016

(87) PCT Pub. No.: WO2015/080629
PCT Pub. Date: Jun. 4, 2015

(65) Prior Publication Data
US 2016/0376634 A1 Dec. 29, 2016

(30) Foreign Application Priority Data
Nov. 28, 2013 (RU) ................ 2013152864

(51) Int. Cl.
*A61K 38/57* (2006.01)
*C07K 14/435* (2006.01)
*C07K 14/81* (2006.01)
*C12Q 1/56* (2006.01)
*G01N 33/86* (2006.01)

(52) U.S. Cl.
CPC ............... *C12Q 1/56* (2013.01); *A61K 38/57* (2013.01); *C07K 14/435* (2013.01); *C07K 14/43563* (2013.01); *C07K 14/81* (2013.01); *C07K 14/811* (2013.01); *C07K 14/8135* (2013.01); *G01N 33/86* (2013.01); *G01N 2333/96458* (2013.01)

(58) Field of Classification Search
CPC .... A61K 38/55; A61K 38/57; A61K 39/3955; C07K 14/81; C07K 14/811; C07K 14/8135; C07K 14/43563; C07K 16/36
See application file for complete search history.

(56) References Cited

U.S. PATENT DOCUMENTS

2009/0304685 A1* 12/2009 Pritchard ............... C07K 16/36
                                                                                   424/133.1
2010/0279923 A1 11/2010 Schulte et al.

FOREIGN PATENT DOCUMENTS

BR           0602496 A     2/2008
RU      2011149982 A    11/2013

OTHER PUBLICATIONS

Sequence Alignment—Applicant's SEQ ID No. 1 and BR 200602496 (Run on Aug. 24, 2017).*
Kolyadko et al. A New Highly Selective Factor XIIa Inhibitor Based on Infestin-4. International Journal of Laboratory Hematology. Jun. 2014, Supplement, vol. 36, p. 9, Abstract No. O21.*
Campos et al., 2012, "The Kazal-type inhibitors infestins 1 and 4 differ in specificity but are similar in three-dimensional structure," Acta Crystallogr. D. Biol. Crystallogr., vol. 68 (Pt. 6): 695-702.
English Translation of the International Search Report for PCT/RU2014/000889, dated Mar. 12, 2015.

* cited by examiner

*Primary Examiner* — Jeffrey E. Russel
(74) *Attorney, Agent, or Firm* — Volpe and Koenig, P.C.

(57) ABSTRACT

The present invention relates to medicine, hematology, biotechnology and fundamental biological research; it can be used for diagnostic and research purposes when studying blood coagulation. One of the aspects of the invention is a polypeptide for selective inhibition of contact activation factor XIIa in a sample of blood or plasma, which comprises the sequence of infestin-4 MutB (SEQ ID NO: 1), where this sequence can have modifications outside the area of the inhibitory loop. Another aspect of the invention is a method of studying coagulation in the test sample, which includes bringing the sample into contact with this polypeptide, bringing a coagulation activator into contact with the sample, and measuring the coagulation parameters. Yet another aspect of the invention is a method of blood anticoagulation by this polypeptide for collection purposes and in order to increase the storage time of the sample.

27 Claims, 5 Drawing Sheets

SEQUENCE LISTING

```
<160> NUMBER OF SEQ ID NOS: 4

<210> SEQ ID NO 1
<211> LENGTH: 56
<212> TYPE: PRT
<213> ORGANISM: Artificial Sequence
<220> FEATURE:
<223> OTHER INFORMATION: Infestin-4 mutant MutB

<400> SEQUENCE: 1

Glu Val Arg Asn Pro Cys Ala Cys Thr Arg Asn Phe Val Ala Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45

Gln Arg Ser Asn Val Glu Gln Phe
    50                  55

<210> SEQ ID NO 2
<211> LENGTH: 6
<212> TYPE: PRT
<213> ORGANISM: Artificial Sequence
<220> FEATURE:
<223> OTHER INFORMATION: Synthetic construct, MutB inhibition loop

<400> SEQUENCE: 2

Thr Arg Asn Phe Val Ala
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic construct, Inf4 inhibition loop
```

```
-continued

<400> SEQUENCE: 3

Phe Arg Asn Tyr Val Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic construct, Mut15 inhibition loop

<400> SEQUENCE: 4

Thr Arg Arg Phe Val Ala
1               5
```

HIGH-SELECTIVITY CONTACT ACTIVATION INHIBITOR BASED ON INFESTIN-4

FIELD OF INVENTION

The present invention relates to medicine, and specifically to hematology, and can be used in particular for diagnostic and research purposes when determining coagulation characteristics of blood and its components, as well as in biotechnology and fundamental biological research.

BACKGROUND

Coagulation of Blood Plasma

Blood coagulation is a defensive process in the body, the formation of a fibrin clot being one of its essential components. The fibrin clot is formed as a result of activation of an enzymatic cascade of coagulation factors; many coagulation factors are serine proteases (VIIa, XIIa, XIa, IXa, Xa, thrombin IIa). The enzymatic cascade also involves activated protein C (aPC), a protease activated by thrombin and inactivating coagulation cofactors VIIIa and Va. The cascade is activated by the «extrinsic» pathway for which factor VIIa (fXIIa) and tissue factor (TF, or thromboplastin) are held responsible, or by the «intrinsic» pathway that starts from contact activation of factor XII (fXII, or Hageman factor) (Mann et al. 1990, Blood 76:1-16; Hoffman and Monroe. 2001, Thromb. Haemost. 85:958-965). Contact activation is auto-activation of fXII in case of a blood plasma contact with negatively charged surfaces. fXII is present in blood plasma in its inactive state; when bound with high molecular weight kininogen (HMWK) and plasma prekallikrein, it can be transformed into an active protease, factor XIIa (fXIIa). Any foreign surface, including walls of plastic or glass tubes, stent or catheter walls, etc., can provoke activation of fXII. fXIIa provides proteolytic activation of prekallikrein into its active form, kallikrein, an enzyme responsible, among others, for fibrinolysis system activation, and of the «intrinsic» pathway factor XI into its active form, factor XIa (fXIa) (Ichinose et al. 1986, J. Biol. Chem. 261:3486-3489; Schmaier. 2008, J. Clin. Invest. 118:3006-3009).

Contact Activation Suppression

Suppression of the contact-activated coagulation, which appears in case of contact of a blood or plasma sample (whole blood or blood plasma, including platelet-rich, platelet-poor, or platelet-free plasma) with a foreign surface and prevents the use of the sample for storage, transfusion, or research, is an important issue (Sperling et al. 2009, Biomaterials 30:4447-4456; Streller et al. 2003, J. Biomed. Mater. Res. B Appl. Biomater. 66:379-390). fXIIa is activated in case of blood collection from the circulation, for example: 1) during blood collection into a tube, from the surfaces of needles, ducts, or tube walls, 2) during storage of frozen blood plasma and subsequent plasma thawing, or 3) when using artificial (extracorporeal) blood circulation apparatus, in particular during blood or plasma transfusion. Contact activation during blood collection or thawing of frozen plasma can initiate clotting in the tube, thus preventing the sample processing and coagulation research (Smith et al. 2010, Blood Coagul. Fibrinolysis. 21:692-702; Suontaka et al. 2005, Vox. Sang. 88:172-180). During autotransfusion or repeated blood infusion, the contact pathway activation leads to increased risk of thrombosis. To block blood clotting when using the artificial blood circulation apparatus, the ducts and other surfaces of the apparatus are covered with fXa or thrombin inhibitors, such as heparin, benzamidine, etc. (Hsu. 2001, Perfusion 16:417-428; Gouzy et al. 2006, Biointerphases 1:146-155). The disadvantage of such method of coagulation blocking is that the addition of fXa and thrombin inhibitors does not prevent generation of fXIIa which can initiate clotting after infusion of blood or plasma into the circulation.

The most common way of suppressing coagulation during blood collection is provided by preliminary addition of calcium ions chelators (for example, of sodium citrate, EDTA, etc.) into the collection tube. Chelation of calcium ions blocks membrane-dependent reactions of fX and thrombin activation (Fischer. 2007, Hemodial. Int. 11:178-189). During the coagulation testing, a coagulation activator (in particular, TF or the contact pathway activator) is added into the test sample containing a chelator, and the plasma is recalcified (by adding an excess amount of calcium ions), after which the fibrin clot formation parameters are studied. The method of coagulation suppression by chelator addition shows a number of disadvantages. The article Mann et al. 2007, J. Thromb. Haemost. 5:2055-2061 demonstrated that chelation of calcium ions during blood collection and subsequent sample recalcification modify the dynamics of fibrin clot formation, formation of thrombin, and aggregation of platelets, in comparison with the samples without addition of the chelator. Chelator addition does not suppress activation of fXI and fIX initiated by fXIIa which is formed during blood collection and sample storage (Nossel et al. 1968, J. Clin. Invest. 47:1172-1180; Oller et at 1976, J. Surg. Res. 20:333-340). Thus, when testing the coagulation, in particular the TF-initiated coagulation through the «extrinsic» pathway (considered to be physiological and responsible for the coagulation in the body in normal conditions), the generated fXIIa also provokes coagulation by the contact pathway, introducing unwanted distortions of the research. The contact pathway of activation in such a research is an artifact that can prevent adequate assessment of physiological coagulation effects, lead to increased error and non-conformity of the research results, as well as to the loss of sensitivity to pathological states of coagulation. To suppress the contact activation, avoid appearance of artifacts, and improve the quality of coagulation research, it is necessary to use fXIIa inhibitor during blood collection or preparation of plasma (Luddington and Baglin. 2004, J. Thromb. Haemost. 2:1954-1959). The used contact activation inhibitor must be highly selective: the inhibitor has to lack any impact on the TF-initiated fibrin clot formation and any inhibitory activity against fXIa, fIXa, fXa, and others, at the concentration of the inhibitor in the sample being sufficient for efficient suppression of the contact pathway of coagulation.

Known Contact Activation Inhibitors

A number of fXIIa inhibitors is known in the field, in particular plasma coagulation inhibitors, such as C1-inhibitor or alpha2-macroglobulin (Davis et al. 2008, Mol. Immunol. 45:4057-4063). Protein inhibitors of trypsin which inhibit fXIIa are also well known in the field; these inhibitors were isolated from different organisms, such as bacterium *E. coli* (Ulmer et al. 1995, FEBS Lett. 365:159-163), or plant seeds (Wynn and Laskowski. 1990, Biochem. Biophys. Res. Commun. 166:1406-1410). The inhibitors isolated from plant seeds include corn trypsin inhibitor, or CTI (Hojima et al. 1980, Thromb. Res. 20:149-162), as well as inhibitors from the squash family: Cucurbita maxima trypsin inhibitor, CMTI-III (Krishnamoorthi et al. 1990, FEBS Lett. 273:163-167), Luffa cylindrica trypsin inhibitor, LCTI-III (Ling et al. 1993, J. Biol. Chem. 268:810-814), and others. Some other non-protein fXIIa inhibitors are known (Woodruff et at 2013, J. Thromb. Haemost. 11:1364-1373). However, most of the said inhibitors are non-selective: besides fXIIa, they also inhibit other coagulation factors, making it impossible to use them in the research of fibrin clot formation.

CTI is believed to be the most selective of all existing inhibitors. CTI has been used for inhibiting contact activation in the assays of TF-initiated coagulation in a sample of blood or its component (U.S. Pat. No. 6,403,381, cl. G01N33/86, publ. Jun. 11, 2002), particularly in the global assays of hemostasis, such as thrombin generation test. However, the data regarding insufficient selectivity of CTI, its influence on the blood coagulation system and other systems interacting with coagulation, are known. For example, CTI can delay fibrinolysis, supposedly by inhibiting the tissue activator of plasminogen (Nielsen. 2009, Blood Coagul. Fibrinolysis 20:191-196).

A fXIIa inhibitor infestin-4 (domain 4 of the protein infestin from the midgut of a blood-sucking insect *Triatoma infestans*) that belongs to the family of Kazal-type inhibitors is also known in the field (Campos et al. 2004, FEBS Lett. 577:512-516). The infestin-4 (Inf4) amino acid sequence and X-ray structure are deposited in the Protein Data Bank, reference number 2ERW.

Known Use of Infestin-4 and Disadvantages of Existing Versions of Infestin-4

The article Hagedorn, Schmidbauer et al. 2010, Circulation 121:1510-1517 demonstrated that infestin-4 is a selective fXIIa inhibitor that blocks fXIIa activity in the thrombosis model in vivo and prevents vascular occlusion without affecting hemostasis parameters. The use of infestin-4 as a fusion protein with albumin in treatment and prevention of thrombosis-related diseases was disclosed in U.S. Pat. No. 8,283,319, cl. A61K 38/16, publ. Oct. 9, 2012. However, the disadvantage of infestin-4 is its inhibitory activity against fXa (inhibition constant Ki 53 nM).

Infestin-4 mutant Inf4Mut15 (Mut15) known in the field has an increased selectivity to fXIIa as it does not inhibit fXa (Campos, Souza et al. 2012, Acta Cryst. D68:695-702). The said mutant was selected as the closest analogue of the present invention. From the prior art, we do not know about inhibition selectivity of fXIIa by the said mutant, that is, we do not know if it possesses any inhibitory activity against fXIa, fIXa, fVIIa, thrombin, or aPC. The use of Mut15, among others in the kit for diagnostics of hemorrhagic and thrombolytic diseases by means of measurement of fXIIa concentration in the patient's blood, is known from patent BRPI 0602496-3, cl. A61K 38/36, publ. Feb. 26, 2008, though the said use is not related with diagnostics of diseases by means of measurement of coagulation parameters. Therefore, the high-selectivity fXIIa inhibitor that blocks contact activation during the assay of TF-initiated blood coagulation is not known in the field.

The objective of this invention is to design a high-selectivity fXIIa inhibitor to block contact activation during the assay of blood or plasma coagulation, in particular TF-initiated, as well as during blood or plasma collection and storage.

SUMMARY

One of the aspects of the present invention is a polypeptide for the inhibition of contact activation in a test sample of blood or its product, which comprises the sequence of the infestin-4 mutant MutB (SEQ ID NO: 1) or which substantially corresponds to it, where the said sequence can be modified outside the area of the inhibitory loop and still significantly maintain the activity of the said polypeptide. The infestin-4 mutant MutB is a high-selectivity fXIIa inhibitor possessing higher activity and selectivity than those of the native infestin-4 or Mut15. "Polypeptide which comprises the sequence of the infestin-4 mutant MutB (SEQ ID NO: 1) or which substantially corresponds to it, where the said sequence can be modified outside the area of the inhibitory loop and still significantly maintain the activity of the said polypeptide" within the above definition includes polypeptides with the amino acid sequence comprising the sequence SEQ ID NO:1, as well as the polypeptides with a slightly modified amino acid sequence, as long as these polypeptides substantially retain the inhibitory activity of the «non-modified» polypeptide and these modifications do not affect the Thr9-Ala14 loop. For example, such modifications may include modifications of the N- or C-terminus of the sequence, deletions or insertions of one or several amino acid residues, as well as conservative amino acid replacements, that is, replacements executed within a group of amino acids with similar properties, for example, (1) small, (2) acidic, (3) polar, (4) basic, (5) hydrophobic, or (6) aromatic amino acids.

Such polypeptide can be produced by chemical synthesis or as a recombinant protein, particularly, as a fusion protein. The recombinant form of such polypeptide may be produced through design of an expression plasmid DNA, its transformation into a host cell, expression of a polypeptide comprising a sequence of infestin-4 mutant MutB and encoded by the said DNA, isolation and purification of the said polypeptide. The DNA fragment encoding essentially the same protein can be obtained, in particular, through modification of the nucleotide sequence of the said plasmid DNA, for example, using the method of site-directed mutagenesis.

The "inhibitory activity" as used herein means functional activity against blood coagulation initiated by the contact pathway. Thus, for example, the inhibitory activity can be evaluated in the Activated partial thromboplastin time (APTT) assay.

The "inhibition selectivity" as used herein means the property of the fXIIa inhibitor residing in highly efficient inhibition of fXIIa (inhibition constant of about 1 nM) and absence of substantial inhibition (inhibition constant exceeding by far 1 nM, preferably over 1 µM) of other coagulation proteases, such as factors fXIa, fIXa, fXa, fVIIa, thrombin, and aPC. Native infestin-4 inhibits fXa with a constant of 53 nM (Campos et al. 2004, FEBS Lett. 577: 512-516). At that, the claimed polypeptide comprising the sequence of infestin-4 mutant MutB provides the same efficiency of fXIIa inhibition as the native inhibitor without inhibiting fXa. Thus, the claimed polypeptide demonstrates elevated selectivity towards fXIIa in comparison with native infestin-4.

The «test sample of blood or its product» is whole blood or its products, such as platelet-rich, platelet-poor, or platelet-free plasma. Fractionated plasma from which one or several proteins were depleted, among others, by the method of affinity chromatography, can also become such blood product. The said sample can be obtained from healthy subjects or from subjects that can suffer or do suffer from coagulation disorders, from disorders or deficiencies of the hemostasis system, in particular from hemorrhagic or thrombotic diseases. The sample can also be obtained from patients during surgery or administration of anticoagulant, procoagulant, anti-aggregant, fibrinolytic, or anti-fibrinolytic therapy, etc. The sample can be freshly drawn or frozen. It can also be lyophilized. The sample can contain natural or recombinant proteins as well as other preparations or reagents, including those with hemostatic or fibrinolytic activity.

Another aspect of the invention is the use of the said polypeptide for coagulation testing in the sample, the test including at least one of the following steps, and preferably all those steps: preparation of a sample, bringing it into contact with the said polypeptide and incubating the resulting mixture, bringing the coagulation activator into contact with the sample containing the said polypeptide, and measuring the sample coagulation parameters.

Preparation of a sample for coagulation assay includes collection of blood into a tube containing or not containing an anticoagulant, among others sodium citrate, EDTA, thrombin inhibitor, fXa inhibitor, and others. The process of a blood sample preparation can include the steps of blood purification from cells or cell components, such as red blood cells, leukocytes, platelets, microvesicles, etc. The purification steps can involve filtration or centrifugation. The prepared sample can be frozen for storage and thawed prior to the assay. The sample can also undergo the step of recalcification prior to the assay.

The polypeptide comprising the sequence of an infestin-4 mutant MutB can be contacted with the test sample of blood or its product in a tube, in particular tube for blood collection, or analytical cuvette. The polypeptide can be preliminarily dissolved, dried, or lyophilized, or also adsorbed at surfaces with which the subject's blood or plasma contact during blood collection, test sample preparation, or coagulation assay procedure. Moreover, the polypeptide can be preliminarily dissolved in solution containing salt, buffer agent, in particular 4-(2-oxyethyl)1-piperazineethanesulfonic acid (HEPES), excipient, or stabilizer, in particular polyvinyl pyrrolidone (PVP). In order to efficiently dissolve the said polypeptide in the sample, the obtained mixture of the sample with the polypeptide can be incubated at temperatures from 20° C. to 40° C., preferably at 37° C., for not less than 3 minutes, preferably over 10 minutes. The quantity of the said polypeptide sufficient for efficient inhibition of the contact-activated coagulation can be determined by measuring the polypeptide activity in the normal sample, for example, by the APTT assay. Thus, the quantity of polypeptide sufficient for efficient inhibition of contact activation shall be the one at which the APTT shall increase more than twofold, preferably more than three-fold, in comparison with the APTT in the sample without polypeptide. The sufficient quantity of the said polypeptide can also be determined using the laboratory diagnostic system «Thrombodynamics analyzer T-2» [RU123166 B of Aug. 16, 2012 class G01N33/86; USPTO Pat. app No. 20100261211], in particular by absence of clots far from the coagulation activator in a normal sample within over 15 minutes, preferably over 30 minutes after activation.

A sample of blood or its product containing the said polypeptide can be brought into contact with the coagulation activator through adding into the said sample of a solution containing a coagulation activator, or through layering of the said solution on the sample without mixing. The sample can also be contacted with the surface-immobilized coagulation activator, without mixing the sample with the activator (Fadeeva et al. 2010, Biochemistry (Moscow) 75:827-838). The tissue factor, in particular relipidated tissue factor, can be used as the coagulation activator. The tissue factor can be obtained as a recombinant protein or isolated from organs or tissues, such as brain, placenta, lungs, of some mammals, for example, human, bovine, or rabbit. One of the coagulation factors, such as VIIa, Xa, IIa, IXa, XIa, XIIa, can also be used as an activator.

Measuring the coagulation parameters in the tested sample of blood or its product can be performed in particular using the thrombin generation assay or the thromboelastography assay known in the field, or the laboratory diagnostic system «Thrombodynamics analyzer T-2». The following coagulation parameters can be determined: lag-time of coagulation, clotting time, delay of thrombin generation, time to achieve thrombin maximum, maximal thrombin concentration, thromboelastogram inclination, clot growth velocity, clot size at a fixed moment, presence of clots far from the coagulation activator, clot lysis velocity, and others.

Another aspect of the invention is the use of a polypeptide comprising the sequence of an infestin-4 mutant MutB as an anticoagulant blocking contact activation through bringing the sample of blood or its product into contact with the said polypeptide in order to improve blood collection procedure and to increase the sample storage time.

The polypeptide comprising the sequence of an infestin-4 mutant MutB can be contacted with a sample of blood or its product in a tube, in particular tube for blood collection. The said polypeptide can be preliminarily dissolved, dried, or lyophilized; it can also be adsorbed at surfaces with which the subject's blood or plasma contact during blood collection or test sample preparation. Moreover, the polypeptide can be preliminarily dissolved in a solution containing salt, buffer agent, in particular HEPES, excipient, or stabilizer, in particular PVP.

In order to efficiently dissolve the said polypeptide in the sample of blood or its product, the obtained mixture of the sample with the polypeptide can be incubated at temperatures from 20° C. to 40° C., preferably at 37° C., for not less than 3 minutes, preferably over 10 minutes. The quantity of the said polypeptide sufficient for efficient inhibition of contact activation of the coagulation can be determined by measuring the polypeptide activity in the sample obtained from a healthy donor, for example, using the APTT assay. Thus, the quantity of polypeptide sufficient for efficient inhibition of contact activation shall be the one at which the APTT shall increase more than twofold, preferably more than three-fold, in comparison with the APTT sample without polypeptide. The sufficient quantity of the said polypeptide can also be determined using the laboratory diagnostic system «Thrombodynamics analyzer T-2»[RU123166 B of Aug. 16, 2012 class G01N33/86; USPTO Pat. app. No. 20100261211], in particular by absence of clots far from the coagulation activator in a normal sample within over 15 minutes, preferably over 30 minutes after activation.

Blood can be collected into a tube additionally containing or not containing anticoagulant, among others sodium citrate, EDTA, thrombin inhibitor, fXa inhibitor and others. The process of a blood sample preparation can include the steps of blood purification from cells or cell components.

The sample of blood or its product can be stored as frozen at negative temperatures below 0° C., preferably below −50° C., or as a liquid at positive temperatures around 0° C., or at a temperature from 20° C. to 40° C. The storage process can also include one or more cycles of freezing and thawing the sample. The storage time can be from 10 minutes and over, in particular from one day and over, preferably over one week.

DETAILED DESCRIPTION OF THE PREFERRED EMBODIMENT(S)

Figure 1:
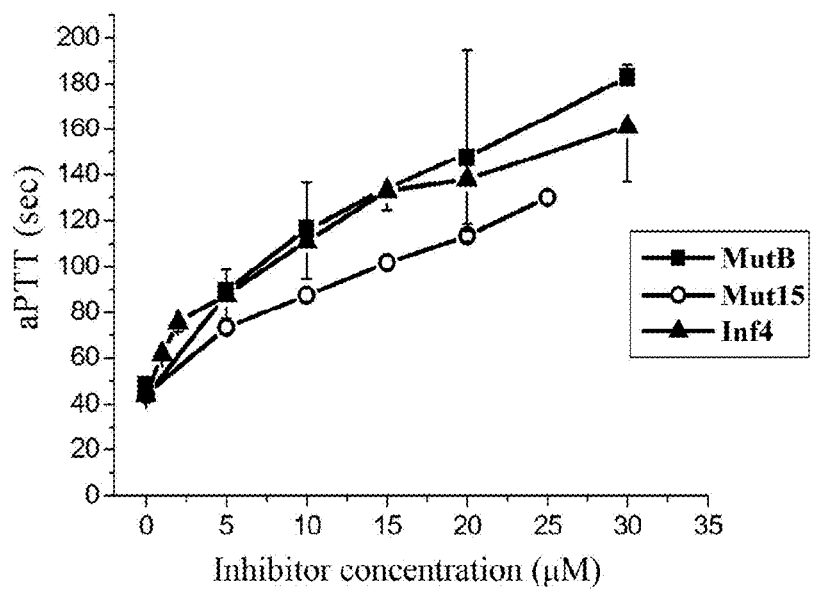
FIG. 1 is a graph showing the dose-dependence of APTT (sec.) on concentration (μM) of the inhibitor, MutB, Mut15 or Inf4, in blood plasma. The average values and standard deviations are given. The number of repeats for MutB and Inf4 n=4; for Mut15 n=2.

Description of a New High-Selectivity Inhibitor of Contact Activation

The claimed polypeptide comprising a sequence of an infestin-4 mutant MutB is a high-selectivity contact activation inhibitor. Amino acid sequence of MutB is included in the list of sequences under the number SEQ ID NO:1. The fXIIa inhibition mechanism is assumed to be competitive: MutB interacts with the active site of fXIIa through the inhibition loop that includes an inhibitor area of Thr9-Ala14; the amino acid sequence of the latter is given in Table 1. Table 1 also includes corresponding sequences of native infestin-4 (Inf4) and known infestin-4 mutant (Mut15). Inside the said area of the inhibition loop, is positioned the reactive site Arg10-Asn11 cleaved in the active site of fXIIa. In Table 1, the amino acid residues included into this area are numbered according to their position as to the reactive site. MutB was generated through introduction of the following amino acid substitutions at the area of the inhibition loop of the native infestin-4: Thr9Phe, Phe12Tyr, and Ala14Pro.

TABLE 1

| Protein | Sequence of the inhibition loop (P$^2$ P$^1$ P$^{1'}$ P$^{2'}$ P$^{3'}$ P$^{4'}$) |
|---|---|
| MutB | TRNFVA (SEQ ID NO: 2) |
| Inf4 | FRNYVP (SEQ ID NO: 3) |
| Mut15 | TRRFVA (SEQ ID NO: 4) |

Selectivity of the New Inhibitor Towards fXIIa

In order to assess selectivity of the fXIIa inhibition by the polypeptide comprising the sequence of the infestin-4 mutant MutB, its inhibitory activity in buffer solution against the purified coagulation factors was determined. The polypeptide's activity was compared with the known fXIIa inhibitors: CTI, infestin-4, infestin-4-based mutant Mut15, LCTI-III. Table 2 shows average values of inhibition constants ($K_i$) of the said proteins against some purified coagulation proteases (fXIIa, fXIa, fXa, and aPC). The standard deviation amounted to about 50% of the average value; each value was measured by performing 2-3 repeats.

TABLE 2

| Protein | fXIIa | fXIa | fXa | aPC |
|---|---|---|---|---|
| MutB | 1 nM | N.I. | N.I. | N.I. |
| CTI | 1 nM | 15 μM | N.I. | 20 μM |
| Inf4 | 1 nM | N.I. | 2 μM | N.I. |
| Mut15 | 1 nM | N.I. | N.I. | 25 μM |
| LCTI-III | 15 nM | 30 μM | N.I. | N.I. | where "N.I." (from "not inhibit") stands for "does not inhibit the enzyme activity".

The data from Table 2 shows that CTI, native infestin-4 and its mutants provide equally efficient inhibition of fXIIa protease activity in the buffer solution. At high concentrations, about tens moles per liter, CTI inhibits both fXIa and aPC, that is, it is not a high-selectivity fXIIa inhibitor. Native infestin-4 and its mutants, such as MutB and Mut15, do not inhibit fXIa. Moreover, infestin-4 mutants MutB and Mut15 do not inhibit fXa, unlike native infestin-4. However, Mut15, like CTI, inhibits activity of aPC, that is, it is not highly selective, too. Table 2 above demonstrates that of all the said fXIIa inhibitors, the inhibitor MutB provides the highest fXIIa inhibition selectivity while it does not demonstrate any inhibition activity against the other said factors.

Assessment of Inhibitory Activity of the New Inhibitor by Suppression of Contact Activation in Blood Plasma The assessment of activity of the polypeptide comprising the sequence of an infestin-4 mutant MutB by its inhibition of the contact-activated coagulation shall be considered further with a reference to FIG. 1. Native infestin-4 and mutants MutB and Mut15 were added into 3 separate samples of platelet free plasma (PFP) of a healthy donor, with subsequent measuring time of contact-activated clotting in the APTT test. The test results allowed drawing dose-dependences of APTT (sec.) on concentration of the added inhibitor (μM), which showed that APTT increased to 120 seconds after addition into the sample of 10 μM MutB, 10 μM native infestin-4, or 20 μM Mut15; at that, without addition of the contact activation inhibitor, APTT was of 45 sec. Thus, MutB was established to have nearly twofold activity in blood plasma in comparison to Mut15.

Figure 2:
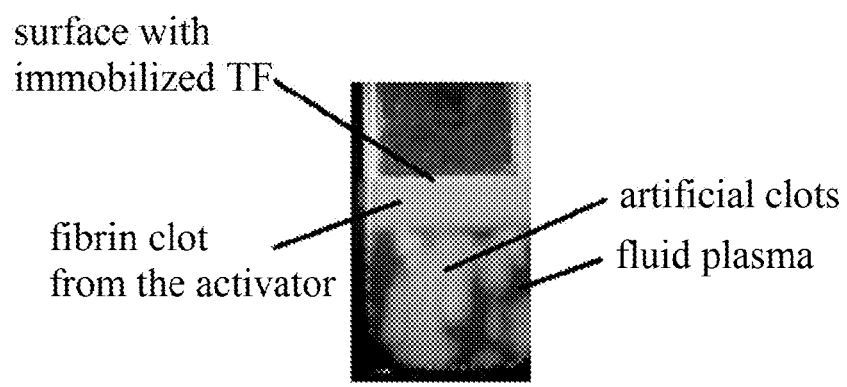
FIG. 2 is a photograph made 30 minutes after activation and showing fibrin clots formed from the activator and the cuvette walls in normal frozen-thawed plasma without adding the contact activation inhibitor.
Figure 3:
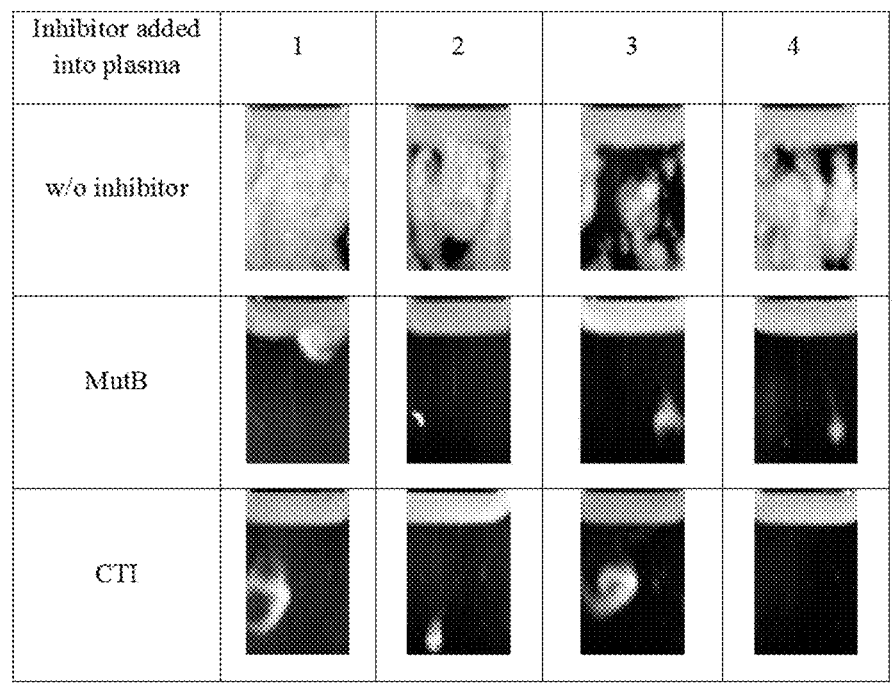
FIG. 3 are photographs made 30 minutes after activation and showing fibrin clots formed in normal frozen-thawed plasma samples with addition of MutB (20 μM), CTI (15 μM), and without adding the contact activation inhibitor (4 repeats for each sample).

Use of the New Inhibitor to Suppress Contact Activation in Assays of TF-Initiated Coagulation The feasibility to use the said polypeptide as the contact pathway inhibitor was demonstrated in a plasma coagulation assay using the laboratory diagnostic system «Thrombodynamics analyzer T-2». The assay included the following steps: thawing of a frozen PFP sample, adding to it of a contact activation inhibitor and incubating the resulting mixture, sample recalcification and its placing into the measuring cuvette channel, bringing the sample into contact with the TF immobilized at the end of a special insert-activator, and detecting the appearance and growth of fibrin clots in the consequent photography mode. The frozen PFP sample was obtained preliminarily through collection of blood into sodium citrate-containing tubes from several (at least five) healthy donors and subsequent 2 stages of centrifugation and freezing of the prepared plasma at −80° C. During the assay arrangement, the fibrin clot was growing from the insert-activator; appearance of additional clots in the cuvette area far from the activator was also possible, as shown on FIG. 2. Clots in the cuvette area far from the activator can be due to the hypercoagulation state of the sample or to the artifacts of sample contact activation from the cuvette walls (artifact clots): the latter must be suppressed for the said test to allow distinguishing between the normal and hypercoagulation states of the coagulation system. To do that, before activating the sample through bringing it into contact with TF, an efficient quantity of the contact activation inhibitor was added into the sample: in this case, we used the polypeptide comprising the sequence of an infestin-4 mutant MutB. To compare the efficiency of the claimed polypeptide comprising the sequence of an infestin-4 mutant MutB with the contact activation inhibitor CTI known in the field, the said inhibitors were added into 2 separate samples of normal frozen PFP plasma. We used such concentrations of the inhibitors at which the APTT increases nearly four-fold: 20 µM in case of MutB and 15 µM in case of CTI. To provide negative test control, we did not add any contact activation inhibitor into the third plasma sample. For each sample, 4 repeated measurements were performed. 30 minutes after the assay start, images of the fibrin clot in measuring cuvettes-4 cuvettes for each sample-were obtained: they are shown on FIG. 3. FIG. 3 shows that addition of either the polypeptide comprising the sequence of an infestin-4 mutant MutB or CTI leads to almost complete suppression of contact activation, preventing formation of artifact clots.

Figure 4:
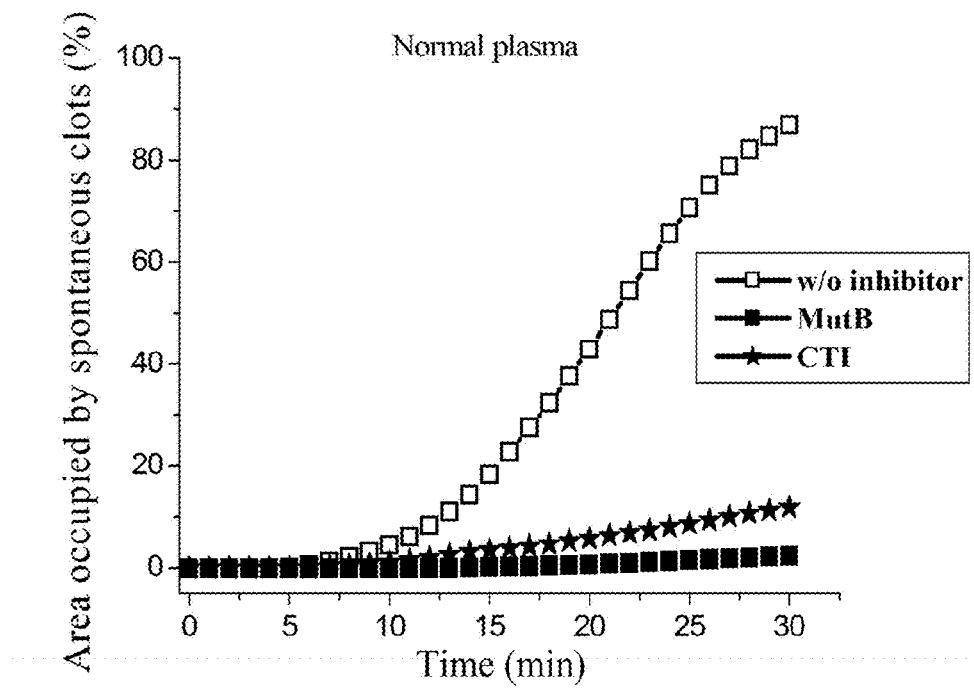
FIG. 4 is a graph showing the time (min.) dependence of the area far from the activator occupied by fibrin clots (% from the cuvette area) in normal frozen-thawed plasma with addition of MutB (20 μM), CTI (15 μM), and without adding the contact activation inhibitor (4 repeats for each sample).

The cuvette area occupied by artifact clots (in % from the total cuvette area; n=4) was plotted for 3 samples of normal frozen plasma at separate time points (FIG. 4, averaged values at each time point). Without adding the contact activation inhibitor, artifact clots appear in the cuvette area far from the activator nearly 15 minutes after activation and occupy the whole cuvette area after 30 minutes. However, after addition of CTI or MutB, such clots occupy not more than 15% of the cuvette area 30 minutes after activation.

Figure 5:
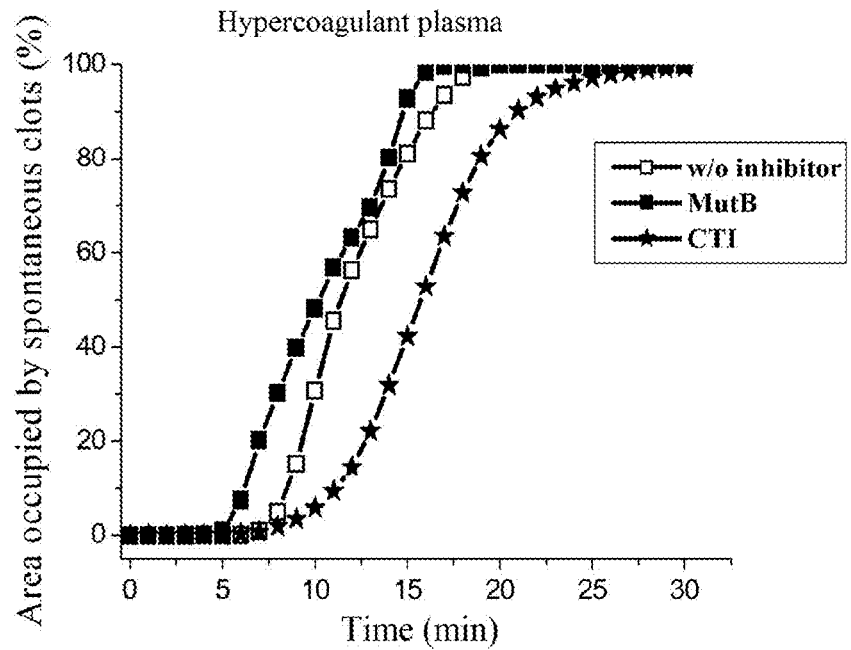
FIG. 5 is a graph showing the time (min.) dependence of the area far from the activator occupied by fibrin clots (% from the cuvette area) in hypercoagulant plasma with addition of MutB (20 μM), CTI (15 μM), and without adding the contact activation inhibitor (4 repeats for each sample).

To assess the influence of the said contact activation inhibitors on appearance, far from the activator, of clots provoked by hypercoagulation, but not by contact activation of the sample by the cuvette walls, we added MutB (20 µM) and CTI (15 µM) into 2 separate samples of hypercoagulant PFP. Hypercoagulant PFP was obtained from normal frozen-thawed PFP by adding 100 pM of fXIa. To provide negative test control, we did not add any contact activation inhibitor into the third plasma sample. FIG. 5 shows time dependences of the cuvette area occupied by the clots far from the activator (in % from the total cuvette area) averaged for 4 repeated experiments. FIG. 5 demonstrates that in hypercoagulant plasma samples without addition of the contact activation inhibitor and with addition of MutB, the clots appeared far from the activator nearly 5-8 minutes after activation, while in the sample with CTI, they appeared after 10-15 minutes.

Thus, we determined that addition of MutB or CTI leads to almost complete suppression of contact activation and prevents formation of artifact clots in normal plasma. However, adding MutB to hypercoagulant plasma does not influence appearance of clots far from the activator: they appear independently from presence of fXIIa, while the addition of CTI delays appearance of clots far from the activator, supposedly due to fXIa inhibition, and can decrease the diagnostic system sensitivity to hypercoagulation.

Consequently, the polypeptide comprising the sequence of an infestin-4 mutant MutB can be used to efficiently block contact activation and contact-activated clotting of blood or its product.

Influence of Contact Activation Inhibitors on Dynamics of Formation of a TF-Initiated Fibrin Clot The influence of contact activation inhibitors on coagulation dynamics can be shown on the example of fibrin clot growth from the surface with immobilized TF. The dynamics of fibrin clot growth from the activator can be characterized by the following parameters: delay of clot formation after the contact of plasma with the tissue factor—lag time (Tlag, min); average clot growth velocity within 2-6 minutes after the start of coagulation—initial velocity (Vin, µm/min); and average clot growth velocity within 15-25 minutes after the start of coagulation—stationary velocity (Vst, µm/min) (Balandina et al. 2011, Biophys. J. 101:1816-1824; Dashkevich et at 2012, Biophys. J. 103:2233-2240). The mentioned parameters allow determining the state of blood coagulation of the subjects from whom the test samples were obtained («Practical coagulology», M A Panteleev, S A Vasilyev, E I Sinauridze and co-authors, ed. by A I Vorobyov. Moscow, publishing house «Practical medicine», 2011, 192 pages., ISBN: 978-5-98811-165-8). Thus, in hypocoagulation states of different origin (deficiency of VII, V, X factors or thrombin, hemophilia A, B, or C, therapy with anticoagulants such as unfractionated or low-molecular heparin, vitamin K antagonists, antithrombin III), the lag time increases while the initial and/or stationary clot growth velocities decrease in relation to normal ranges for healthy donors (Parunov et al. 2011, J. Thromb. Haemost. 9:1825-1834). Hypercoagulation states of different origin provoke appearance of clots in the cuvette area far from the activator, with increase of the initial and/or stationary clot growth velocities in relation to normal ranges. When using a contact activation inhibitor, it is preferable to use an inhibitor that does not influence the formation of clots far from the activator in a sample of hypercoagulant plasma or the dynamics of fibrin clot growth from the activator in any plasma sample.

Figure 6A:
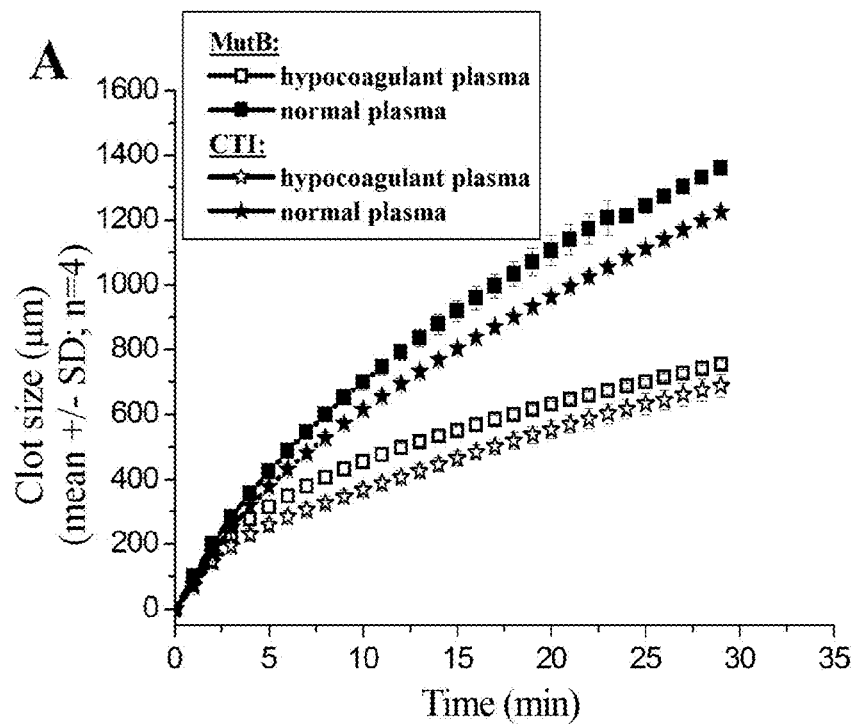
FIG. 6 A-D are graphs showing influence of contact activation inhibitors MutB (20 μM) and CTI (15 μM) on the fibrin clot growth from the activator into a bulk of normal and hypocoagulant frozen-thawed plasma.
Figure 6B:
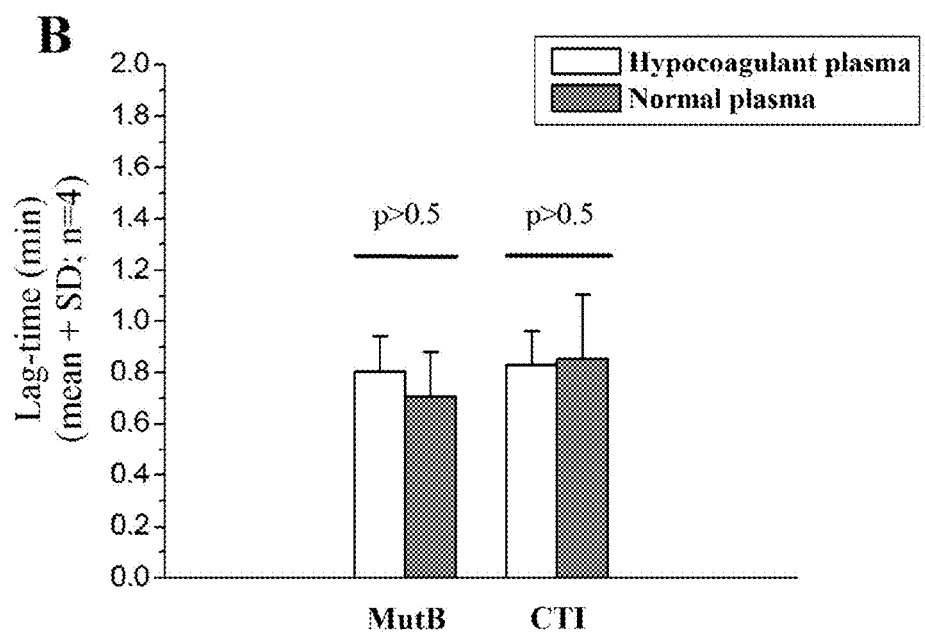
Figure 6C:
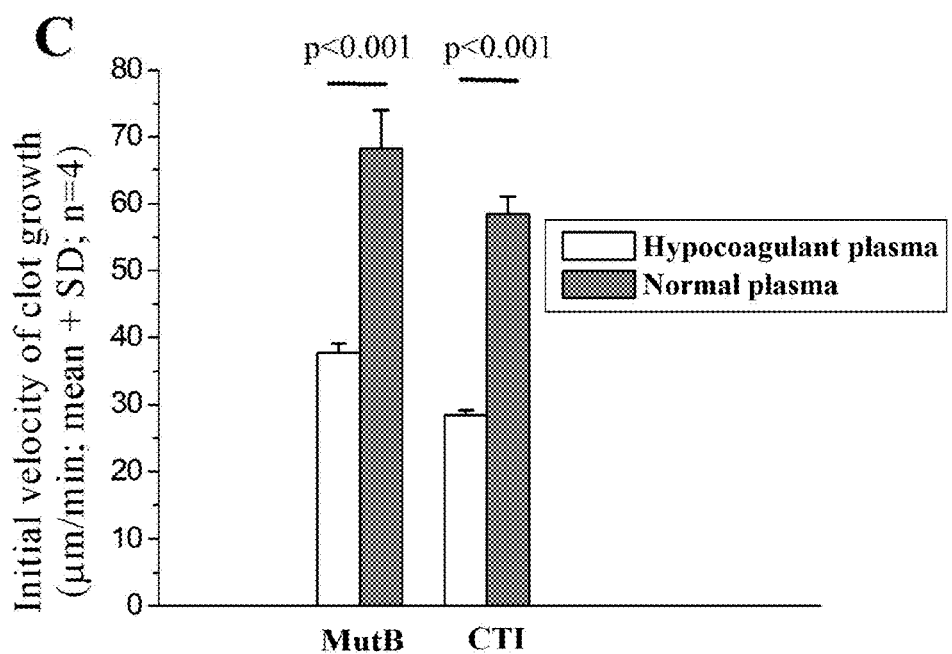
Figure 6D:
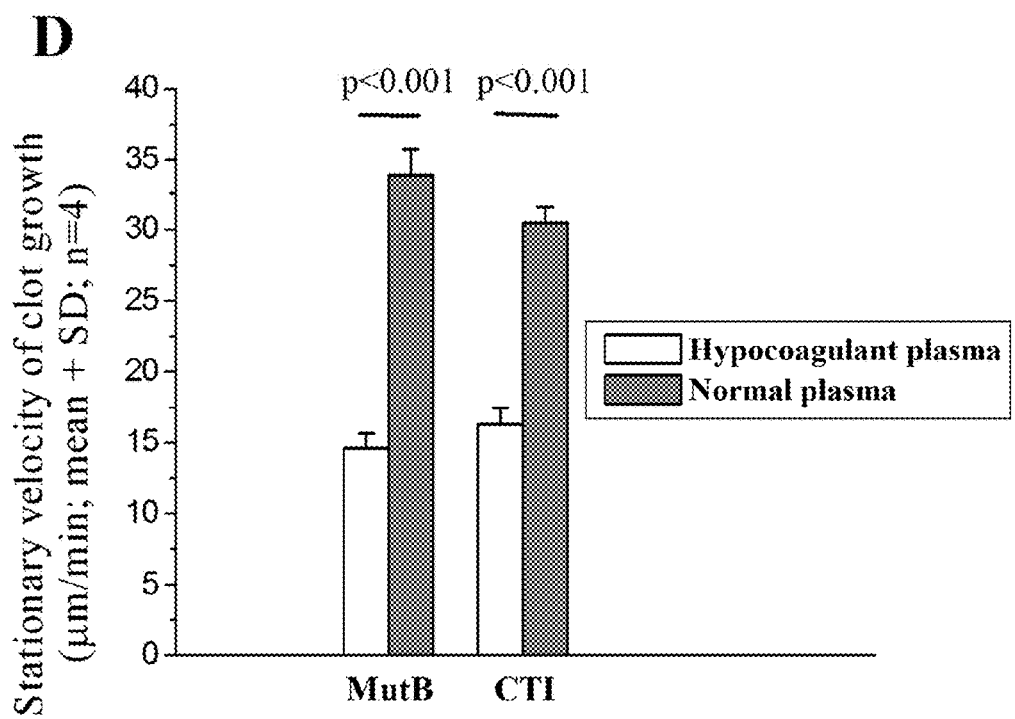

The influence of contact activation inhibitors MutB and CTI on sensitivity of the fibrin clot growth parameters towards hypocoagulation was compared by adding MutB (20 µM) and CTI (15 µM) into 2 samples of normal frozen PFP and 2 samples of hypocoagulant PFP. Hypocoagulant PFP was obtained from normal frozen PFP by adding 0.1 IU/ml of unfractionated heparin. FIG. 6A shows the time (min.)-dependent growth of the fibrin clot (µm) averaged for 4 repeated experiments for the samples of hypocoagulant and normal plasma with added inhibitors MutB and CTI. Bar graphs also show the average values +/− standard deviation (S.D.) for 4 repeated measurements of the following clot growth parameters: lag time (FIG. 6B), initial velocity (FIG. 6C), and stationary velocity (FIG. 6D). The Student's test was used for statistical comparison. Statistical significance of differences of the clot growth parameters in hypocoagulant and normal plasma is designated as «p<0.001». Insignificant differences are designated as «p>0.5».

FIG. 6A demonstrates that in the samples of hypocoagulant and normal plasma, the dynamics of fibrin clot growth is significantly different, though adding of MutB or CTI does not have any influence on this difference. The lag time (Tlag) parameter does not change after addition of heparin into plasma (FIG. 6B), though at that, clot growth velocities decrease nearly twofold (FIG. 6C, D).

Use of the New Inhibitor as an Anticoagulant for the Purposes of Collection and Storage of Whole Blood The feasibility to use the polypeptide comprising the sequence of an infestin-4 mutant MutB as an anticoagulant during collection and storage of the whole blood was demonstrated by measuring the time of spontaneous clotting in the tube containing MutB (10 µM), CTI (5 µM), or not containing any contact activation inhibitor. We used concentrations of contact activation inhibitors leading to 2.5-fold increase of APTT in normal plasma. Untreated whole blood was collected from 3 healthy donors without adding any anticoagulant, for example, citrate, except for the said contact activation inhibitors. The blood was mixed with the said inhibitors at 22° C. using a rotator, after which the time of clot formation in the blood was measured.

Figure 7:
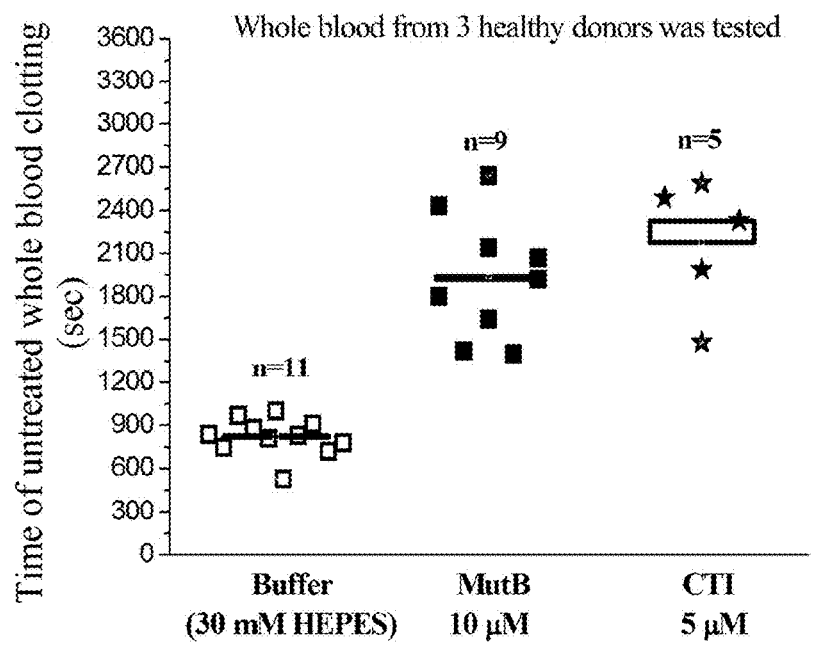
FIG. 7 is a graph showing the clotting time (sec.) of the whole blood collected from 3 healthy donors; the whole blood was either untreated or mixed with MutB (10 μM) or CTI (5 μM) (2-4 repeats for each donor).

FIG. 7 shows the results of measurements where each dot corresponds to one measurement; lines or rectangles indicate the median values of the resulting clotting times. FIG. 7 demonstrates that the use of a contact activation inhibitor MutB or CTI during blood collection without the calcium ions chelator allows two to three-fold increasing of the whole blood storage time in the tube.

Thus, we demonstrated the advantage of use of the polypeptide comprising the sequence of an infestin-4 mutant MutB, a new high-selectivity contact activation inhibitor, for prevention of clotting by the contact pathway in a plasma sample and increasing of the diagnostic system sensitivity to hemostasis deviations from the normal state.

The aspects of this invention are described in the following examples provided only to illustrate this invention and help a person having ordinary skill in the art to implement and use it. The examples are in no case intended to confine the scope of the invention.

EXAMPLES

From this point on, this invention shall be illustrated but not confined by the following examples. However, the materials, methods, etc. described here shall only illustrate the invention aspects and are in no case intended to confine the scope of the invention. Therefore, the materials, methods, etc. similar or equivalent to those described herein can be used for material implementation or testing of the present invention.

Example 1. Selectivity of MutB as Related to fXIIa in a Buffer Solution

To determine the inhibition activity of such proteins as MutB, CTI, Inf4, Mut15, and LCTI-III as related to different coagulation proteases in a buffer, the chromogenic test was used: the mixture of protease and inhibitor was incubated in the wells of the plate for 15 minutes at 37° C., after which the chromogenic substrate solution was added to the mixture, and the protease activity was measured as the rate of chromogenic product formation at 37° C. Table 3 shows names and concentrations of chromogenic substrates and the corresponding proteases.

TABLE 3

| Protease | Protease concentration in the test, nM | Substrate | Substrate concentration in the test, mM | $K_M$ of substrate to protease, mM |
|---|---|---|---|---|
| fXIIa | 1 | S-2302 | 0.2 | 0.2 |
| fXIa | 0.1 | S-2366 | 0.5 | 1.0 |
| fXa | 0.5 | S-2765 | 0.5 | 0.25 |
| aPC | 1 | Spectrozyme pCa | 0.2 | 0.4 |

Chromogenic substrates included a p-nitroanilide group cleaved by the corresponding proteases. After cleavage of the p-nitroanilide group from the substrate molecule, the group absorption spectrum changes, and the change of concentration of such product within time can be detected at the light wavelength of 405 nm using a plate spectrophotometer. To build a dependence curve of the protease activity from the inhibitor concentration, different inhibitor concentrations were added into several samples with the same protease concentration. After that, the inhibitor concentration able to decrease the protease activity by 50% (IC50) was determined. The inhibition constant Ki was calculated using the Cheng-Prusoff equation (Ki=IC50/(1+S/KM)), where S is the initial substrate concentration, KM is the Michaelis-Menten constant of the substrate to the protease. The results of Ki calculation are given in Table 2.

Native infestin-4 and its mutants MutB and Mut15 used here were fusion proteins with thioredoxin I E. coli containing polyhisticline clusters. In general, thioredoxin I E. coli and polyhistidine clusters are secondary polypeptide areas without influence on its activity, well known in the field and used to increase the level of expression of the soluble target proteins and to purify them, correspondingly. CTI was a protein isolated from corn and purified using the chromatographic method. LCTI-III was a chemical synthesis product. The substrate cleavage reaction was administered in a buffer of 50 mM Tris-HCl, 130 mM NaCl, 0.5% bovine serum albumin, pH 8.3.

Example 2. Assessment of MutB Inhibition Activity in Suppression of Contact Activation in the Blood Plasma Blood plasma from healthy donors was processed according to standard protocols of blood collection for coagulation assays (Collection, Transport, and Processing of Blood Specimens for Testing Plasma-Based Coagulation Assays and Molecular Hemostasis Assays; Approved Guideline Fifth Edition by Clinical and Laboratory Standards Institute (CLSI) H21-A5 Vol. 28 No. 5). 0.38% sodium citrate was added into blood to block the calcium ions.

The APTT test was administered using the reagent kits "Coagulo-test" (Scientific-production association Renam, Moscow, Russia) and different concentrations of the following contact activation inhibitors: native infestin-4, MutB, and Mut15. To do that, 50 microliters of blood plasma from a healthy donor were mixed with 5.6 microliters of a 10× solution of different inhibitor concentrations and incubated for 15 minutes at 37° C. Then, according to the "Coagulo-test" manual, 25 microliters of the mixture were transferred into the cuvette of the coagulometer Helena-C2, with addition of 25 microliters of kaolin-cephalin mixture activating fXII in blood plasma. After incubation at 37° C. for 3 minutes, 25 microliters of the calcium chloride solution in the initial concentration of 25 mM was added, and the time of fibrin clot formation in the coagulometer cuvette was determined photometrically.

APTT dependences on concentrations of native infestin-4, MutB and Mut15 obtained in the same way as in Example 1, are shown on FIG. 1. The infestin-4 mutant MutB was established to have increased activity in blood plasma in comparison with Mut15 and native infestin-4.

Example 3. MutB Influence on Appearance of Artifact Clots Due to Contact Activation and on Dynamics of Growth of a TF-Initiated Fibrin Clot The influence of a polypeptide consisting of the sequence of an infestin-4 mutant MutB on the growth of fibrin clots in the samples of hypocoagulant, normal, and hypercoagulant blood plasma was studied using the laboratory diagnostic system «Thrombodynamics analyzer T-2» and the «Diagnostic kit for thrombodynamics investigation in blood plasma» (HemaCore, Moscow, Russia) according to the manual to the «Diagnostic kit for thrombodynamics investigation in blood plasma» (HemaCore, Moscow, Russia). Here, the said polypeptide was preliminarily proteolytically cleaved and chromatographically purified from thioredoxin (Trx). 15 minutes before the assay, the measuring cuvette, insert-activator with immobilized TF, and the reagents were held at 37° C. Standard investigation temperature was of 37° C. 15 minutes before the assay, 120 microliters of plasma were mixed with the investigated substances, MutB or CTI, for comparison, and put into a microtube. After mixing of the plasma with the substances, the tube with the plasma was put into a thermostat at 37° C. for 15 minutes. Immediately before the assay, the plasma was re-calcified: 120 microliters of the mixture of plasma and substances were put into a microtube with Reagent II (lyophilized solution of calcium acetate with an additive), and mixed up to complete Reagent II dilution. Then, 120 microliters of the mixture with Reagent II from the microtube was immediately transferred into the measuring cuvette. After that, the insert-activator was carefully inserted into the cuvette so that the surface with immobilized tissue factor would contact the plasma. Immediately after the contact of the coagulation activator with the blood plasma, the photography of the process of fibrin clot growth in plasma within the cuvette started. The cuvette-activator was a plate with the coagulation activator—tissue factor—immobilized at the low end surface (Fadeeva et al. 2010, Biochemistry (Moscow) 75:827-838). The automatic calculation of the assay results was performed using the software (user manual «Software for the laboratory diagnostic system «Thrombodynamics analyzer T-2», HemaCore, Moscow, Russia).

Example 4. Increase of the Whole Blood Storage Time in Case of Blood Collection without Calcium Chelator and with MutB Blood was collected from the median cubital vein of the left hand into a sterile syringe Master UN PE, volume 10 ml, needle 21 G×1½"; 0.8×40 mm (FarmLine, USA). Calcium chelator or other anticoagulants, except contact activation inhibitors MutB or CTI, were not added into plasma. Here, MutB also did not contain thioredoxin. The collected blood was poured into a 15 ml tube, mixed by inverting it twice, after which 0.7 ml portions of blood were poured into 1.5 ml polypropylene microcentrifuge tubes MaxyClear Snaplock (Axygen, USA); immediately after, time record using a stopwatch started. Preliminarily, 78 microliters of MutB solution at 100 µM concentration, CTI solution at 50 µM concentration, or buffer solution of 30 mM Hepes pH 7.4 were added into the said tubes. The tubes containing the mixture of whole blood with the said solutions were fixed in the rotator and mixed by inverting them at the rotation speed of 10 rpm. The time of appearance of clots or fibrin filaments in the whole blood during mixing was fixed.

What is claimed is:

1. A polypeptide for inhibition of contact activation in a test sample of blood or plasma comprising the sequence of an infestin-4 mutant MutB having SEQ ID NO: 1 or a variant thereof, wherein the variant thereof comprises modifications in an amino acid sequence outside the inhibition loop of the polypeptide and maintains the inhibitory activity of the polypeptide; and wherein the polypeptide is a high-selectivity fXIIa inhibitor with selectivity or inhibitory activity higher than that of the native infestin-4 or Mut15.

2. The polypeptide according to claim 1, wherein the modifications are selected from the group consisting of: modifications of the amino acid residues at the N- or C-terminus of the sequence of SEQ ID NO:1, deletions or insertions of one or several amino acid residues, and conservative amino acid replacements.

3. A method for assessing coagulation in a test sample comprising blood, platelet-rich plasma, platelet-poor plasma, fractionated plasma, or plasma, including:
   a) preparing a test sample comprising combining blood, platelet-rich plasma, platelet-poor plasma, fractionated plasma, or plasma and the polypeptide of any one of claim 1 or 2 to obtain a mixture and incubating the mixture for a period of time, wherein incubating prevents or suppresses spontaneous coagulation of blood or plasma via the contact pathway;
   b) adding a blood coagulation activator to the mixture of step a), wherein addition of the blood coagulation activator initiates coagulation in the mixture; and
   c) assessing parameters of the coagulation initiated in step b).

4. The method according to claim 3, wherein preparing the test sample includes blood collection into a tube containing an anticoagulant selected from the group consisting of: sodium citrate, EDTA, thrombin inhibitor, and fXa inhibitor, and wherein the method further comprises blocking of the anticoagulant.

5. The method according to claim 4, wherein preparing the test sample further includes filtration or centrifugation of the tube to separate cells or cell components from blood.

6. The method according to claim 3, wherein blood or plasma is freshly drawn, or lyophilized or frozen, and is transformed into liquid form prior to the step of preparing the test sample.

7. The method according to claim 6, wherein the test sample comprises blood.

8. The method according to claim 3, wherein the test sample is obtained from a healthy subject or a subject suffering from a blood coagulation disorder, hemorrhage or thrombosis.

9. The method according to claim 3, wherein the test sample is obtained from a patient during surgical interventions or administration of a therapy.

10. The method according to claim 3, wherein the test sample contains exogenously added natural or recombinant proteins or other preparations with hemostatic or fibrinolytic activity.

11. The method according to claim 3, wherein the polypeptide is dried, lyophilized, adsorbed at a surface contacting the test sample, or dissolved in solution containing salt, buffer agent, excipient, or stabilizer prior to the step of preparing.

12. The method according to claim 3, wherein the incubation temperature of the mixture is a temperature in the range from 20° C. to 40° C., and the time period is at least 3 minutes.

13. The method according to claim 3, wherein the step of combining comprises adding the polypeptide in a quantity sufficient to block contact activation.

14. The method according to claim 13, wherein the sufficient quantity is a quantity of the polypeptide capable of increasing the normal plasma APTT at least twofold in comparison to plasma APTT without the polypeptide.

15. The method according to claim 13, wherein the sufficient quantity is a quantity of the polypeptide at which artifact clots far from the coagulation activator in normal plasma are absent over 15 minutes after activation.

16. The method according to claim 3, wherein the blood coagulation activator is a dissolved coagulation activator, and wherein the step of adding comprises mixing the dissolved coagulation activator with the mixture of step a).

17. The method according to claim 3, wherein the blood coagulation activator is a dissolved coagulation activator and adding comprises layering the dissolved coagulation activator onto blood or plasma of the mixture of step a) without mixing, or wherein the blood coagulation activator is an activator immobilized on a surface, and adding comprises contacting the mixture of step a) with the activator immobilized on the surface.

18. The method according to claim 3, wherein the blood coagulation activator is a tissue factor or one of the coagulation proteases selected from the group consisting of: VIIa, Xa, IIa, IXa, XIa, and XIIa.

19. The method according to claim 3, wherein the coagulation parameters are selected from the group consisting of: lag-time of coagulation, clotting time, delay of thrombin generation, time to achieve thrombin maximum, maximal thrombin concentration, thromboelastogram inclination, clot growth velocity, clot size at a fixed moment, presence of clots far from the coagulation activator, and clot lysis velocity.

20. A method for improving a blood collection procedure comprising bringing a sample of blood or plasma into contact with the polypeptide of claim 1 or 2, wherein the contact causes blocking of contact-activated coagulation and increases the test sample storage time.

21. The method according to claim 20, wherein the polypeptide is dried, lyophilized, adsorbed at a surface contacting the sample dissolved in a solution containing salt, buffer agent, excipient, or stabilizer.

22. The method according to claim 20, wherein blood is collected into a tube containing an anticoagulant selected from the group consisting of: sodium citrate, EDTA, thrombin inhibitor, and fXa inhibitor.

23. The method according to claim 20, wherein the sample is stored frozen at a temperature below 0° C. or stored as a liquid at a temperature in a range from 0° C. to 40° C.

24. The method according to claim 20, wherein the storage time is over 10 minutes.

25. The method according to claim 20, wherein the sample is obtained from a healthy subject.

26. The method according to claim 6, wherein the test sample comprises a platelet-rich, platelet-poor, or fractionated plasma.

27. The method according to claim 20, wherein the sample is obtained from a subject suffering from coagulation disorders, a subject with hemorrhage or thrombosis, or a subject during surgical interventions or administration of a therapy.

\* \* \* \* \*